United States Patent
Salla et al.

(10) Patent No.: US 7,367,953 B2
(45) Date of Patent: May 6, 2008

(54) METHOD AND SYSTEM FOR DETERMINING A PERIOD OF INTEREST USING MULTIPLE INPUTS

(75) Inventors: Prathyusha K. Salla, Waukesha, WI (US); Gopal B. Avinash, New Berlin, WI (US); Cherik Bulkes, Sussex, WI (US)

(73) Assignee: GE Medical Systems Global Technology Company, Waukesha, WI (US)

( * ) Notice: Subject to any disclaimer, the term of this patent is extended or adjusted under 35 U.S.C. 154(b) by 516 days.

(21) Appl. No.: 10/723,858

(22) Filed: Nov. 26, 2003

(65) Prior Publication Data

US 2005/0113702 A1 May 26, 2005

(51) Int. Cl.
*A61B 5/02* (2006.01)
(52) U.S. Cl. .................................................. 600/508
(58) Field of Classification Search ........... 600/508, 600/513, 528; 607/18, 20
See application file for complete search history.

(56) References Cited

U.S. PATENT DOCUMENTS

| | | | |
|---|---|---|---|
| 4,712,560 A * | 12/1987 | Schaefer et al. | 600/413 |
| 4,994,965 A * | 2/1991 | Crawford et al. | 378/95 |
| 5,701,897 A * | 12/1997 | Sano | 600/453 |
| 6,358,208 B1 * | 3/2002 | Lang et al. | 600/438 |
| 2004/0260346 A1 * | 12/2004 | Overall et al. | 607/4 |

* cited by examiner

*Primary Examiner*—George Manuel
(74) *Attorney, Agent, or Firm*—Fletcher Yoder

(57) ABSTRACT

One or more techniques are provided for identifying a period of minimal motion for an organ of interest, such as the heart or lungs. Motion data is acquired for the organ of interest and for one or more proximate organs using sensor-based and/or image-based techniques. The sensor-based techniques may include electrical and non-electrical techniques. The image-based techniques may include both pre-acquisition and acquisition image data. The motion data for the organ of interest and proximate organs may be used to generate a set of multi-input motion data that may be processed to identify desired periods, such as periods of minimal motion, within the overall motion of the organ of interest.

27 Claims, 4 Drawing Sheets

METHOD AND SYSTEM FOR DETERMINING A PERIOD OF INTEREST USING MULTIPLE INPUTS

BACKGROUND OF THE INVENTION

The present technique relates generally to the measurement of the overall motion undergone by an object. More specifically, the present technique relates to identifying a period of interest in the motion of an object within a complex system using multiple sources.

Both living and mechanical complex systems may be formed from the combination of an assortment of components. In the case of living systems, the components may be the various organs and tissues that comprise the body of an organism. In the case of a mechanical system, the components may be the various parts forming the working mechanism of the system. In these types of complex systems a variety of the components may be located on the interior of the system, such as within the organism or mechanism body, where they are not subject to easy observation or examination.

Furthermore, the interior components may move relative to one another and to the exterior of the system. For example, in the context of a living organism, organs, such as the heart, lungs, diaphragm, stomach, and so forth, may move independent of one another (such as the heart and stomach) or in conjunction with one another (such as the lungs and diaphragm). Similarly, mechanical complex system may have interior moving parts, such as rotors, turbines, levers, arms, pistons, valves, and so forth, which, depending on the mechanism of operation, may move independent of or in conjunction with one another.

The difficulty in observing the interior components of such moving systems may make it difficult to observe the synchrony, or lack thereof, of the moving components. Furthermore, as one might expect, the motion of one interior component may contribute to the overall motion of connected or proximate interior components. The overall motion of a component may be difficult to ascertain without knowing the motion of all possible contributors to the overall motion. For example, in the context of the living organism, the motion of the heart may be of interest for various reasons, including diagnostic imaging or interventional procedures. The overall motion of the heart, however, may not be simply attributable to cardiac contractions but may also be attributable to respiration, i.e., lung and diaphragm motion, to skeletal muscular contractions, or to other proximate muscular motions. Similarly, within a mechanical system, the overall motion of a component, such as a turbine, may be attributable not only to the motion of the component itself but may also be attributable to other proximate moving components which are operating independent of or in conjunction with the component of interest.

In some cases, the overall motion of a component may be of interest, not simply the motion attributable to the component. For example, in a mechanical system, the overall motion of an internal component may indicate a problem, such as a component moving outside of the tolerance range, or a pending problem or failure, such as a vibration or stressful motion indicating the pending breakage or failure of a component. Similarly, in a living organism, the overall motion of an organ, such as the heart or lungs, may be of interest for imaging or interventional purposes, such as to perform motion correction or artifact correction.

Determining the overall motion of a component may be difficult, however. In particular, sensors or component specific information sources may only provide information about one aspect of the overall motion of a component. For example, in the case of a turbine, internal sensors may only report a measure, such as RPM, which provides information about the rotation of the turbine, but no information about proximate moving components that may be moving the turbine incidental to their own motion.

Similarly, in the context of a living organism, it may be desirable to know the overall motion of the heart. Techniques such as electrocardiography (ECG), however, only provide information regarding the cardiac phase of the heart, i.e., what state of contraction the heart is in at a point in time. Information such as the motion of the respiratory organs, i.e., the lungs and/or diaphragm, which may contribute to the overall motion of the heart, is not captured by a technique, such as ECG, which simply ascertains information about the contractions of the heart. It may, therefore, be desirable to characterize the overall motion undergone by an internal component of a complex system for analysis of the system.

BRIEF DESCRIPTION OF THE INVENTION

The present invention is directed to a technique for a period of interest in the overall motion of one or more component of a complex system. The overall motion of the component or components of interest may be determined from a set of multi-input motion data. The multi-input motion data may comprise motion data for the component of interest derived from multiple sources, such as sensor-based or image data-based sources. The multi-input motion data may also comprise motion data for proximate components, which contribute to the overall motion of the component of interest, derived from one or more sources, including possibly a source used to measure the component of the organ -of interest. The multi-input nature of the multi-input motion data, therefore, may describe either the presence of motion data for more than one component, the presence of multiple sources of motion data for a component, or the presence of both multi-input and multi-source motion data.

The multi-input motion data may be used to determine one or more periods of interest for the component of interest, such as a quiescent period corresponding to an interval of minimal overall motion for the organ. An interval such as a quiescent period may be used, such as in a medical imaging context, to determine gating points that may used to gate image data, prospectively and/or retrospectively, to reduce motion artifacts in the resulting image. In addition, a quiescent period or other period of interest may be used to derive one or more motion compensation factors which may be applied during image processing to reduce motion artifacts. Other periods of interest may include a particular phase of motion associated with one or more motion cycles or periods, such as the onset of cardiac contraction in medical imaging.

In accordance with one aspect of the present invention, a technique is provided for identifying one or more periods of minimal motion for a heart. In view of this aspect, at least one set of electrical data representative of cardiac motion and at least one set of non-electrical data representative of cardiac motion may be acquired. A set of multi-input motion data comprising the sets of electrical and non-electrical data may be generated. One or more periods of minimal motion for the heart may be extracted from the set of multi-input motion data. Systems and computer programs that afford functionality of the type defined by this method are also provided by the present technique.

In accordance with another aspect of the present invention, a technique is provided for identifying one or more periods of minimal motion. In view of this aspect, at least one set of non-electrical data representative of cardiac motion and one or more sets of data representative of respiratory motion may be acquired. A set of multi-input motion data comprising the set non-electrical data representative of cardiac motion and the one or more sets of motion data representative of respiratory motion may be generated. One or more periods of minimal motion for one of a heart and a respiratory organ may be extracted from the set of multi-input motion data. Systems and computer programs that afford functionality of the type defined by this method are also provided by the present technique.

In accordance with a further aspect of the present invention, a technique is provided for identifying one or more periods of minimal motion. In view of this aspect, at least one set of electrical data representative of cardiac motion, at least one set of non-electrical data representative of cardiac motion, and one or more sets of data representative of respiratory motion may be acquired. A set of multi-input motion data comprising the set of electrical data representative of cardiac motion, the set non-electrical data representative of cardiac motion, and the one or more sets of motion data representative of respiratory motion may be generated. One or more periods of minimal motion for one of a heart and a respiratory organ may be extracted from the set of multi-input motion data. Systems and computer programs that afford functionality of the type defined by this method are also provided by the present technique.

BRIEF DESCRIPTION OF THE DRAWINGS

The foregoing and other advantages and features of the invention will become apparent upon reading the following detailed description and upon reference to the drawings in which.

DETAILED DESCRIPTION OF SPECIFIC EMBODIMENTS

Figure 1:
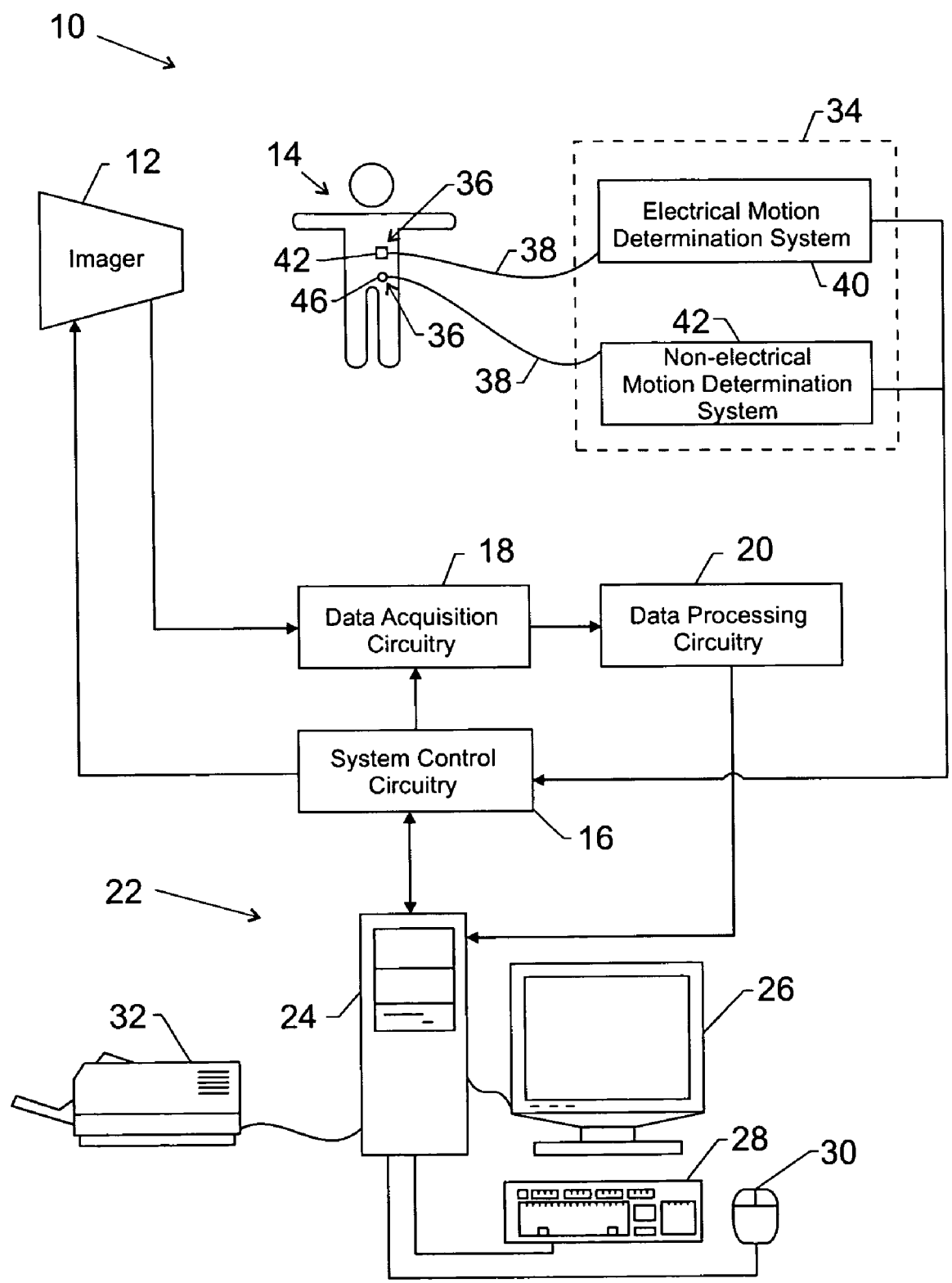
FIG. 1 is a general diagrammatical representation of certain functional components of an exemplary generic imaging system capable of gating and/or motion correction via the present technique.

In the field of complex systems, including complex mechanical and living systems, it may be desirable to characterize the motion of one or more internal components of the system that cannot be directly observed. Often a measure of the intrinsic motion of a component may be available, such as RPM for a turbine or rotating component or ECG for a heart. Such measures, however, may not convey the overall motion of the component of interest, but may instead convey only a part of the overall motion, that part attributable to the component itself. The present technique is directed to measuring the overall motion of an internal component of a complex mechanical or living system. For the purpose of explanation, an example of the present technique will be provided in the context of living complex systems. In particular, the example discusses the technique as it may be applied in the field of medical imaging.

In the field of medical imaging, it is often desirable to characterize the motion of an imaged organ so that the motion may be accounted for to improve image quality. Measures of the muscular activity of the organ of interest, however, may characterize only a portion of the overall motion of the organ relative to the viewer or imaging scanner. In particular, the overall motion may consist of not only the muscular contractions of the organ of interest itself, i.e., the intrinsic motion, but also motion attributable to the movement of proximate organs. For example, the overall motion of the heart may consist of not only the muscular contractions of the heart but also the movement of the respiratory organs, i.e., the lungs, and/or diaphragm, or other proximate muscular contractions, voluntary and/or involuntary, of the patient's body. Therefore, in the example of cardiac imaging, it may be desirable to characterize the overall motion of the heart relative to the imager, not simply the motion attributable to the contraction of the heart itself.

For example, the motion of the organ to be imaged may be used in image acquisition or reconstruction techniques that rely on data gating. In general, data gating techniques acquire image data (prospective gating) or select acquired image data (retrospective gating) based upon the motion of the organ being imaged, allowing image data to be acquired or selected at or near the desired phase of motion. The acquired or selected image data may then be reconstructed to form images that have fewer artifacts attributable to organ motion.

However, to the extent that the gating process relies only upon information related to the muscular contraction or movement of the organ of interest, the process may not account for the motion component attributable to other proximate organs. In other words, the overall motion of the organ of interest may not be accounted for by looking at the muscular activity of the organ of interest alone. Failure to account for the overall motion of the organ of interest during gating may result in reconstructed images containing motion related artifacts.

One way in which the overall motion of the organ of interest may be determined is to employ one or more motion determination techniques capable of determining the motion of the organ of interest more precisely and/or to determine the motion of one or more proximate organs that contribute to the overall motion of the organ of interest. These multiple inputs of motion data may be analyzed, such as by various combination and/or separation techniques, to determine one or more quiescent periods for the organ of interest in which the overall motion of the organ is minimized relative to the imager. The quiescent periods may then be used to gate the imaging process, either prospectively or retrospectively, to generate images of the organ of interest with reduced or minimal motion artifacts.

Alternatively, other desired periods may be selected based upon the multiple inputs. For example, a period may be selected in which the motion of proximate organs, such as the lungs, is minimized, while the heart is at an active phase of the cardiac cycle, such as the initiation of contraction. In this way the, motion affects attributable to proximate organs may be minimized, while a cardiac phase of interest may be imaged.

Similarly, if multiple motion inputs are used to measure the cardiac motion, such as electrical and mechanical sensors, a period may be selected based upon specific combination motion inputs. For example, a period may be of interest where the electrical activity, measured by electrical sensors, indicates cardiac muscle depolarization, but the mechanical activity, measured as displacement, acceleration, etc., is not indicative of the expected muscular motion. In this manner, periods of interest marked by specific or signature characteristics may be pinpointed and imaged or the respective image data selected from a larger set of image data for processing. As one of ordinary skill in the art will appreciate, one or more of the multiple inputs may be derived from the imaging modality itself, such as motion data derived from pre-acquisition imagining sequences, such as Navigator pulses or scout images, or from acquisition data, whether in unreconstructed or reconstructed form. In this manner, sensory and/or imaging data may be used to derive the motion data comprising the multiple inputs.

An exemplary imaging system 10 capable of operating in accordance with the present technique is depicted in FIG. 1. Generally, the imaging system 10 includes some type of imager 12 that detects signals and converts the signals to useful data. As described more fully below, the imager 12 may operate in accordance with various physical principals for creating the image data. In general, however, the imager 12 creates image data indicative of the region of interest in a patient 14, either in a conventional support, such as photographic film, or in a digital medium.

The imager 12 operates under the control of system control circuitry 16. The system control circuitry 16 may include a wide range of circuits, such as radiation source control circuits, timing circuits, circuits for coordinating data acquisition in conjunction with patient or table movements, circuits for controlling the position of radiation sources and detectors, and so forth. In the present context, the system control circuitry 16 may also include memory elements, such as magnetic or optical storage media, for storing programs and routines executed by the system control circuitry 16 or by associated components of the system 10. The stored programs or routines may include programs or routines for performing all or part of the present technique.

Image data or signals acquired by the imager 12 may be processed by the imager 12, such as for conversion to digital values, and provided to data acquisition circuitry 18. The data acquisition circuitry 18 may perform a wide range of processing functions, such as adjustment of digital dynamic ranges, smoothing or sharpening of data, as well as compiling of data streams and files, where desired. In situations where pre-acquisition image data, such as Navigator pulses in magnetic resonance imaging (MRI), are acquired, the data acquisition circuitry 18 may provide image data to the system control circuitry 16 for prospective gating.

The data acquisition circuitry 18 may also transfer acquisition image data to data processing circuitry 20, where additional processing and analysis are performed. The data processing circuitry 20 may perform substantial analyses of image data, including ordering, sharpening, smoothing, feature recognition, and so forth. In addition, the data processing circuitry 20 may receive motion data for one or more organs from one or more sensor-based motion detection systems 34, as discussed in detail below. Based on image-based and/or sensor-based motion data, gating and/or motion compensation may be facilitated by the data processing circuitry 20, such as by determining gating intervals and/or motion corrections factors that may be provided to the system control circuitry 16 and/or operator workstation 22. The processed image data may be stored in short or long term storage devices, such as picture archiving communication systems, which may be located within or remote from the imaging system 10 and/or reconstructed and displayed for an operator, such as at the operator workstation 22.

In addition to displaying the reconstructed image, the operator workstation 22 may control the above-described operations and functions of the imaging system 10, typically via an interface with the system control circuitry 16. The operator workstation 22 may include one or more processor-based components, such as general purpose or application specific computers 24. In addition to the processor-based components, the operator workstation 22 may include various memory and/or storage components including magnetic and optical mass storage devices, internal memory, such as RAM chips. The memory and/or storage components may be used for storing programs and routines for performing the techniques described herein that are executed by the operator workstation 22 or by associated components of the system 10. Alternatively, the programs and routines may be stored on a computer accessible storage and/or memory remote from the operator workstation 22 but accessible by network and/or communication interfaces present on the operator workstation 22.

The operator workstation 22 may also comprise various input/output (I/O) interfaces, as well as various network or communication interfaces. The various I/O interfaces may allow communication with user interface devices, such as a display 26, keyboard 28, mouse 30, and printer 32, that may be used for viewing and inputting configuration information and/or for operating the imaging system 10. The various network and communication interfaces may allow connection to both local and wide area intranets and storage networks as well as the Internet. The various I/O and communication interfaces may utilize wires, lines, or suitable wireless interfaces, as appropriate or desired.

As one of ordinary skill in the art will appreciate, more than a single operator workstation 22 may be provided for an imaging system 10. For example, an imaging scanner or station may include an operator workstation 22 which permits regulation of the parameters involved in the image data acquisition procedure, whereas a different operator workstation 22 may be provided for manipulating, enhancing, and viewing results and reconstructed images.

The motion of one or more organs of interest may be detected and/or measured in a variety of ways and provided to the imaging system 10. As one of ordinary skill in the art will readily apprehend, the type of data gating desired may determine the type of motion data acquired. In some cases, the motion data of interest may be derived using the image scanner 12 itself. For example, pre-acquisition imaging techniques, such as navigator pulses in MR systems, scout images in CT systems or fluoroscopic images in other generalized X-ray applications, may be employed to determine the motion of the organ of interest or other organs proximate to the organ of interest. In other cases, motion data for the organ or organs of interest may be determined from the acquisition image data in the acquired, i.e., unreconstructed, domain and/or in the reconstructed domain. Use of the imaging system 10 to acquire motion data, both in the pre-acquisition and the acquisition context, are examples of image-based motion detection and measurement, as discussed in detail herein.

In some instances, however, sensor-based motion determination techniques may be employed. In these instances, the exemplary imaging system 10 may include or may be in communication with one or more sensor-based motion determination systems 34. The sensor-based motion determination systems 34 typically comprise one or more sensors 36 in the form of a pad or contact that may be disposed on skin surface of the patient 14. The contact area of a sensor 36 may vary in size from micrometers to centimeters in diameter and height. The size selected is usually based on an application. Similarly, the number of sensors 36 used may depend on the application.

When disposed on the patient 14, the sensor 36 may detect and/or measure some metric or parameter of interest, such as an electrical or mechanical event, that may be used as an indicator of organ motion. The sensor 36 may be connected to the respective sensor-based determination system 34 via one or more leads 38 which may transmit a signal representative of the sensed metric or parameter to the respective system 34 for processing. In some contexts, the sensor 36 may communicate with the respective sensor-based motion determination system 34 via wireless means, such as a wireless network protocol, as opposed to a physical lead 38.

Sensor-based determination systems 34 may include electrical motion determination systems 40, such as systems that detect or measure electrical activity or characteristics of an organ to indicate motion. Electrical motion determination systems 40 may measure electrical activity indicative of the muscular contractions of an organ, such as an electrocardiogram (ECG). Electrical motion detection systems 40 may also measure changes in electrical properties, such as impedance, which are indicative of organ motion, such as impedance plethysmography. The electrical sensors 42 used to detect electrical events, such as electrical contact pads, are typically strategically placed to detect the electrical attributes of the organ. For example, in the context of detecting and monitoring the motion of the heart, electrical events can be detected by a four-sensor ECG system, a twelve-sensor ECG system, a vector cardiography (VCG) type of arrangement, or by multiple ECG sensors arranged in array or matrix format to cover the region of interest.

Sensor-based motion determination systems 34 may also include non-electrical motion determination systems 44, such as systems that detect and/or measure displacement, acceleration, velocity, pressure, and/or other mechanical indicators of motion. Various types of mechanical sensors 46 may be employed to detect and/or measure the mechanical indicators of motion, including accelerometers, optical markers, displacement sensors, force sensors, ultrasonic sensors, strain gauges, photodiodes, and pressure sensors.

The non-electrical events may be detected one or more mechanical sensors 46. In the case of multiple mechanical sensors 46, the mechanical sensors 46 may be arranged in an array or matrix format placed in or near the region of interest. Sensor arrays or configurations are possible in which the mechanical sensors 46 are arranged in a three-dimensional matrix such that the entire body surface in the region of interest is covered, such as by using a suit or wrap. Typically, in an array of mechanical sensors 46 used to measure non-electrical events, the mechanical sensors 46 are placed equidistant from each other. For instance, a δ unit of separation may be maintained between the mechanical sensors 46 in the X, Y, and/or Z directions.

In general, the mechanical sensors 46 of a non-electrical motion determination system 44 detect the mechanical, i.e., physical, motion of the organ or organs of interest via one or more of the means listed above. For example, internal movement, such as a heart beat or respiration, may create mechanical motion detectable by one or more mechanical sensors 46 disposed on the skin of the patient 14 as pressure, displacement, acceleration, and so forth. In this manner, internal motion of one or more internal organs may be detected, measured, and represented, either as a map of surface motion or as a map of internal motion. Such a map of surface or internal motion may be combined with other sensor or image data to generate a fusion image representing the various measured characteristics, such as structure, acceleration displacement, and/or electrical activity.

Figure 2:
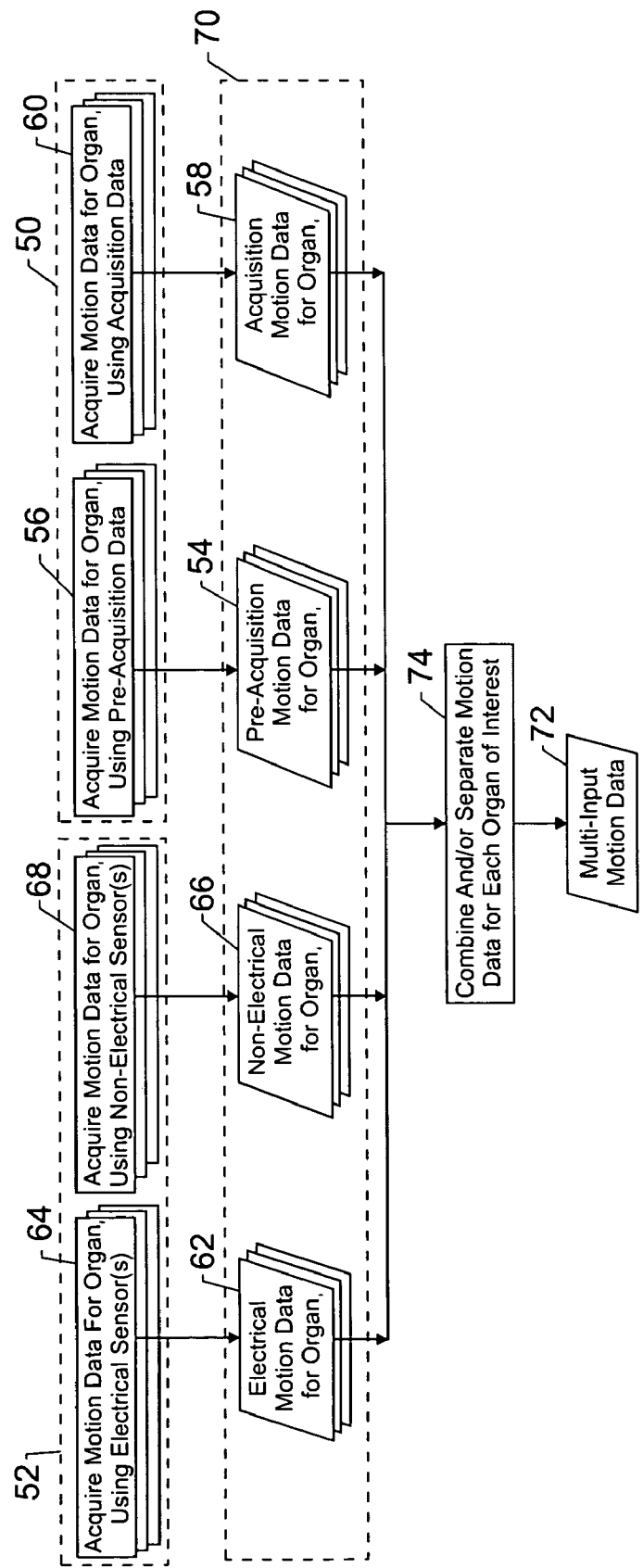
FIG. 2 is a flowchart depicting the acquisition of a multi-input motion data set, in accordance with the present technique.

Image-based and sensor-based motion detection and measurement using the various systems and components of FIG. 1, is described in detail with reference to FIG. 2. Detection and/or measurement of the motion of one or more organs may occur via a variety of processes and at different times prior to, during or after the imaging process. In particular, image-based detection and/or measurement of organ motion, as depicted by block 50, and/or sensor-based detection and/or measurement of organ motion, as depicted at block 52, may occur at suitable times within the process. Due to this time independence, the various motion measurement and/or detection techniques may be performed in a variety of orders or concurrently, depending on the constraints of the technique, with the resulting motion data representing the data available at any given time. For example, within the category of image-based techniques 50, motion may be detected and/or measured by using pre-acquisition motion data 54, as determined at block 56, and/or by using acquisition motion data 58, as determined at block 60.

Examples of pre-acquisition techniques for detecting or measuring motion of one or more organs, as depicted at step 56, include the use of navigator echoes in MRI, the use of scout images in CT, and the use of fluoroscopic images in other X-ray contexts. Pre-acquisition motion detection and measurement typically involves determining the position of the organ or organs of interest by a pre-acquisition measurement using the imaging system 10. Subsequent image acquisition can then occur during similar states of organ motion or subsequently acquired image data may be selected for processing and reconstruction based upon a similar state of organ motion.

For example, in MRI, a navigator echo pulse is a quick MR pre-pulse sequence that measures the position of an organ, such as the diaphragm, before primary image data acquisition. The pre-pulse sequence images a narrow area perpendicular to the movement of the organ of interest, i.e., a vertical area for a diaphragm. The contrast of the moving interface is typically high to permit easy automatic detection. Once the pre-acquisition motion data 54 has been acquired, the position of the interface may be recorded and imaging data may be acquired or selected based on whether the position of the interface falls within a range of pre-specified values determined from the pre-acquisition data 54. Using the navigator echo data, similar respiratory rates or other motion states of the patient can be identified and used for motion estimation. Hence, the navigator echo technique may be used as a respiratory gating technique that does not utilize additional sensing equipment, as the MR system itself provides the sensing.

Similarly, acquisition motion data 58, such as organ motion information derived from the unreconstructed and/or reconstructed image domains, may be used to determine the motion of one or more organs. The acquisition motion data 58 may be determined from one-dimensional, two-dimensional, or three-dimensional representations of the imaged region derived from the image data. For example, organ motion may be determined in the unreconstructed image domain after a segmentation or structure identification step. Changes in the location of the segmented structure or region may be determined in sequential image date and equate to the motion of the organ or organs. In this manner, acquisition motion data 58 may be used to determine motion for one or more organs in the field of view of the imager 12.

Likewise, within the category of sensor-based techniques 52, motion of one or more organs may be determined using electrical motion data 62, as determined at block 64, and/or by using non-electrical motion data 66, as determined at block 68. The electrical motion data 62 may include ECG data if the heart is an organ of interest, or impedance plethysmography data if the lungs are an organ of interest. Electrical signals or properties of other organs of interest may also comprise the electrical motion data provided suitable electrical sensors 42 are disposed on the patient 14.

In regard to non-electrical motion data 66, the motion of virtually any organ may generate mechanical or physical indicia that may be detected or measured by suitable mechanical sensors 46 disposed on the skin of the patient 14. For example, accelerometers may comprise the mechanical sensors 46 for measuring acceleration, and the respective displacement, resulting from the motion of an internal organ, such as the heart, lungs, stomach, liver, pancreas, and so on. Similarly, ultrasonic sensors, optical markers, strain gauges, and so forth may be deployed as mechanical sensors 46 suitable for measuring acceleration, displacement, velocity, pressure, and other non-electrical motion data 62 associated with one or more organs.

The aggregate motion data 70, i.e., the motion data for each organ for which motion was detected or measured and/or for each motion sensing methodology employed, contains the multi-input motion data 72 of interest for the imaging process. Aspects of the aggregate motion data 70 may be combined and/or separated for each organ of interest or for the different motion sensing methodologies, as depicted at block 74, to derive the multi-input motion data 72 relevant for the organs or organs of interest at a given time or point in the process. The combination and/or separation procedure depicted may depend on the number of organs of interest, the techniques employed to measure motion, the coverage area of the imaging modality, the processing techniques to be employed, i.e., prospective and/or retrospective, and so forth. For example, where the motion of an organ is measured or detected by multiple motion sensing methodologies, the motion information may be combined to derive a more accurate motion characterization of the organ at a given time. Similarly, where a motion sensing methodology detects the motion of more than one organ, the information associated with each organ may be separated to better characterize the motion of the individual organs at a given time. The result of the combination and/or separation procedure 74 is one or more sets of multi-input motion data 72 which may be used for motion compensation in respective images and/or may be subsequently analyzed to obtain prospective or retrospective gating intervals for image acquisition and processing.

In this manner, the multi-input motion data 72 may comprise motion data for the organ of interest derived from multiple sources, such as sensor-based or image data-based sources. The multi-input motion data may also comprise motion data for proximate organs, which contribute to the overall motion of the organ of interest, derived from one or more sources, including possibly a source used to measure the motion of the organ of interest. The multi-input nature of the multi-input motion data, therefore, may encompass either the presence of motion data for more than one organ, the presence of multiple sources of motion data for an organ, or the presence of both multi-organ and multi-source motion data.

Furthermore, positional information may be taken into account, such as during data acquisition, combination and/or separation, or during subsequent processing, to generate the multi-input motion data 72. For example, an initial determination may be made whether the coverage area of the sensors 36 or of the imager 12 is sufficient to cover the desired region of interest. If the coverage area is sufficient, motion detection and/or measurement and image processing may proceed as discussed above.

However, if the coverage area is insufficient, such as when scans or images are being taken of the torso from the neck to the abdomen or of the whole body, positional sensors may be employed. The positional sensors may provide information concerning the region being currently scanned so that other data acquisition activities may be activated or deactivated accordingly. For example, when positional sensors are employed, the sensors 36 in the area being scanned by the imager 12 may be activated while sensors 36 outside of the scanned area may remain inactive. In this manner, unnecessary or redundant data is not acquired. As one of ordinary skill in the art will appreciate, the number of positional sensors may vary depending on the application. Alternatively, the sensors 36 may all be active during the image data acquisition. The positional information obtained by the positional sensors, however, may be employed during the combination and/or separation step 74, or during subsequent processes, to discard unnecessary image or motion data or to otherwise account for the positional information during imaging.

Figure 3:
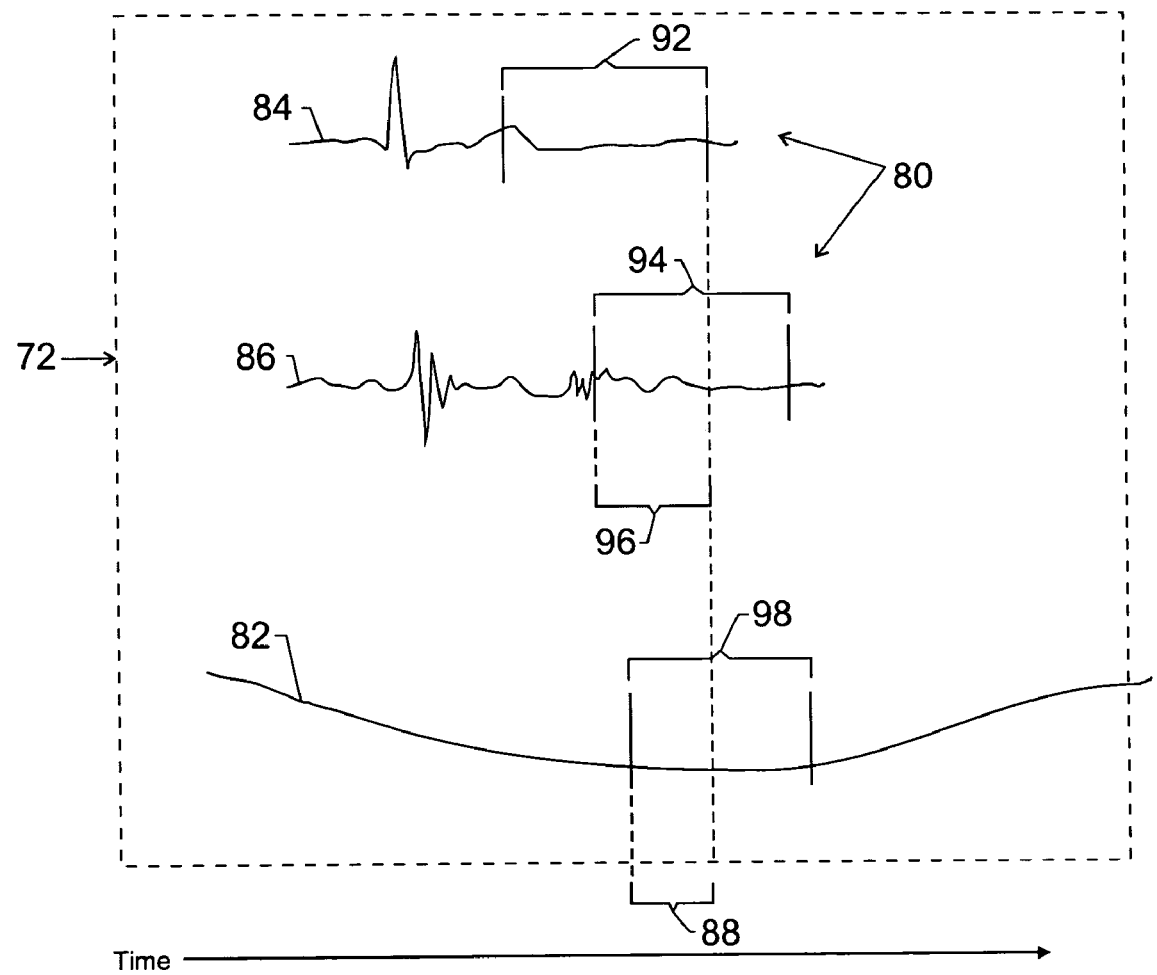
FIG. 3 is an exemplary representation of a multi-input motion data set and of a common gating period derived from the multi-input motion data.

An example of a set of multi-input motion data 72 is depicted in FIG. 3. As depicted in FIG. 3, the multi-input motion data 72 includes three waveforms, two cardiac motion waveforms 80 and a pulmonary motion waveform 82. The cardiac waveforms include an ECG 84 and a mechanical cardiogram (MCG) 86, such as may be derived using one or more mechanical sensors 46 disposed on the skin that measure cardiac acceleration and/or displacement. The pulmonary motion waveform 82 may be derived by electrical means, such as impedance plethysmography, or by non-electrical means, such as by the acceleration or displacement measured by one or more mechanical sensors 46. Indeed, the same mechanical sensors 46 may be used to measure both heart and lung motion with the motion data associated with each organ being separated to form the multi-input motion data 72.

Figure 4:
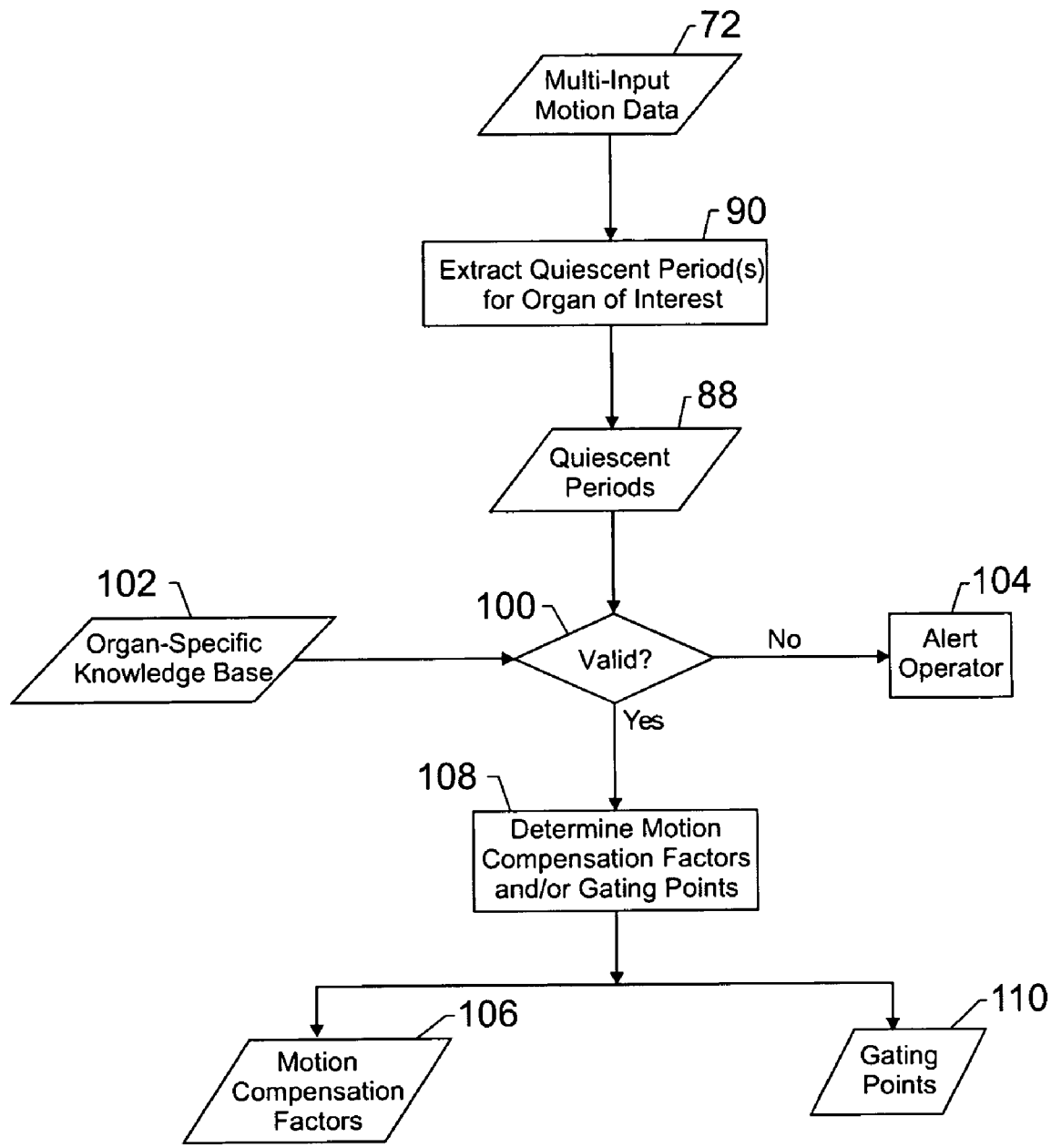
FIG. 4 is a flowchart depicting the determination of gating points and/or motion compensation factors from a set of multi-input motion data.

In the context of gating techniques, the multi-input motion data 72 may be processed to extract one or more quiescent periods 88 for the one or more organs of interest, as depicted at step 90 of FIG. 4. Referring once again to FIG. 3, this extraction process can be visualized with reference to the cardiac waveforms 80 and the pulmonary waveform 82. For example, referring to the ECG waveform 84, an interval of minimal motion 92 can be distinguished from the ECG 84 between the T wave and the subsequent P wave. Similarly, an interval of minimal motion 94 can be distinguished from the MCG 86 roughly coincident with the interval 92 determined from the ECG 84. A cardiac interval of minimal motion 96 which reflects the interval common to the ECG interval 92 and the MCG interval 94 can thereby be derived from the cardiac waveforms 80. Similarly, a pulmonary interval of minimal motion 98 can be derived from the pulmonary waveform 82.

A quiescent period 88 that reflects the interval common to the cardiac interval of minimal motion 96 and the pulmonary interval of minimal motion 98 may thereby be derived. In the context of the present example, the quiescent period 88 represents an interval of minimal motion for all of the organs represented by the multi-input motion data 72. As one of ordinary skill will appreciate, additional quiescent periods 88 may be similarly derived. Furthermore, additional motion data for these organs and/or for other or additional organs may be included within the multi-input motion data 72. In particular, the generation and/or processing of the multi-input motion data set 72, such as in the separation/combination step 78 and/or in the extraction step 90, can be performed for each individual organ separately, in series, in parallel, or in any order for use in subsequent processes and analyses.

As a validation step or as an additional step in the process, the organ motion from a second source, such as from motion computed in either one-dimension or two-dimensions from the unreconstructed or reconstructed acquisition image data may be used for validation. In this manner, organ motion derived from the acquisition image data can be synergistically used to determine one or more quiescent periods 88 or to validate the quiescent periods 88 determined by sensor-based and/or pre-acquisition image data-based techniques, as depicted at decision block 100. In addition, the one or more quiescent periods 88 may be tested for validity based on organ specific knowledge 102 pertaining to the one or more organs of interest, such as may be obtained from a general physiological reference work or database, or based on patient specific factors, such as patient history. If the quiescent period 88 is determined not to be valid based on the image-based motion information and/or the organ or patient specific knowledge, an operator may be alerted that no quiescent period 88 can be extracted, as depicted at block 104, and acquisition or processing may be terminated or modified.

If the one or more quiescent periods 88 are determined to be valid, the validated quiescent periods 88 may be used to determine motion compensation factors 106, as depicted at step 108. Determination of one or more motion compensation factors 106 may involve modeling the anticipated motion, based on the multi-input motion data 72 and/or quiescent periods 88, and calculating factors that compensate for the motion. Motion modeling can be accomplished either using the data directly or using a priori information about the moving organ. When motion is computed directly from the data, motion compensation factors 106 may be derived by an iterative algorithm trying to optimize criteria in multiple domains including the spatial and transform domains. When prior information is available, non-iterative methods can be used for determination of motion compensation factors 106.

Gating points 110 may be derived from the validated quiescent periods 88 at step 108 instead of, or in addition to, motion compensation factors 106. The gating points 110 typically describe the points in time from which acquired data is selected, for retrospective gating, or during which data acquisition occurs, for prospective gating. For example, referring to FIG. 3, gating points 110 may be selected which coincide with the beginning and end of the quiescent period 88 such that image data is acquired or selected at the beginning of the quiescent period 88 and is not selected or acquired after the end of the quiescent period 88. In this manner, image data is acquired or selected which corresponds to an interval of low or no motion for the organ of interest, such as the heart or lungs in this example. Reconstructed images of the organ or organs of interest, therefore, should be less susceptible to motion-related artifacts.

Though the preceding discussion relates the derivation and use of one or more quiescent periods 88, other periods of interest may be derived and, therefore, substituted for the quiescent period 88. For example, as discussed above, the desired period of interest may correspond to a minimized phase of motion for one organ, while a second organ is at a phase of motion in which motion is not minimized. In this manner, the effects of the motion of a proximate organ may be minimized while emphasizing the desired phase of motion, such as the initiation of a contraction, of the second organ. Similarly, motion signatures may be used to select the desired phase of motion. For example, inconsistencies between the multiple motion inputs may indicate a problem condition that may be of interest. For example, electrical data indicative of a contraction acquired concurrently with mechanical data that does not demonstrate the expected contraction may represent a period of interest. Such signatures may of course vary depending on the event of interest and upon the parameters being measured.

While the preceding discussion and example relates to living complex systems and medical imaging in particular, one of ordinary skill in the art will appreciate that the technique may be employed in the context of other complex systems, such as mechanical systems. For example, complex mechanical systems may include numerous moving components disposed on the interior of the system. As with a living organism, the motion of these various components may contribute to the overall motion of a particular component of interest. To the extent that it is desirable to know the overall motion of the component of interest or to identify particular periods of interest, such as motion signatures that may indicate potential failure, the present technique may be employed.

For example, mechanical sensors 46 that measure displacement, acceleration, and so forth, may be useful indicators of vibration, rotation, frequency, and so forth, associated with one or more internal components of a complex mechanical system. Similarly, electrical sensors 42 may measure, electrical and/or magnetic field strength, resistance, impedance, and so forth, associated with one or more internal components of a complex mechanical system. Similarly, non-invasive imaging techniques may be employed to acquire image data that may be processed to provide motion data inputs to the multi-input process discussed herein. By means of these various motion determining methodologies, a multi-input set of motion data may be generated and processed, as described with respect to FIGS. 2 and 4, to identify a period of interest associated with one or more of the dynamic components.

Based upon the identified period of interest, the complex system may be operated or serviced, depending on the significance of the period. For example, a period of interest selected based upon a multi-input signature associated with a pending failure of fault condition, may indicate the need for servicing. In this manner, maintenance of a system or performance of a component of a system may be determined using multi-input motion data.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

What is claimed is:

1. A method for identifying one or more periods of minimal motion, comprising the steps of:

acquiring at least one set of electrical data representative of cardiac motion, at least one set of non-electrical data representative of cardiac motion, and one or more sets of data representative of respiratory organ motion;

generating a set of multi-input motion data comprising the set of electrical data representative of cardiac motion, the set non-electrical data representative of cardiac motion, and the one or more sets of motion data representative of respiratory organ motion; and extracting one or more periods of minimal motion for one of the heart and the respiratory organ from the set of multi-input motion data.

2. The method, as recited in claim 1, wherein the one or more sets of data representative of respiratory motion comprise at least one of a set of electrical data representative of respiratory motion and a set of non-electrical data representative of respiratory motion.

3. The method, as recited in claim 1, wherein the set of multi-input motion data further comprises one or more sets of motion data for one or more proximate organs.

4. The method, as recited in claim 1, wherein the step of acquiring comprises measuring a set of electrical data representative of cardiac motion using electrical sensors.

5. The method, as recited in claim 1, wherein the step of acquiring comprises measuring a set of non-electrical data representative of cardiac motion using mechanical sensors.

6. The method, as recited in claim 1, wherein the step of acquiring comprises measuring a set of electrical data representative of respiratory motion using electrical sensors.

7. The method, as recited in claim 1, wherein the step of acquiring comprises measuring a set of non-electrical data representative of respiratory motion using mechanical sensors.

8. The method, as recited in claim 1, wherein the step of acquiring comprises measuring one of cardiac motion and respiratory motion from one or more images.

9. The method, as recited in claim 8, wherein the one or more images are derived from one of pre-acquisition image data, unreconstructed acquisition image data, and reconstructed acquisition image data.

10. The method as recited in claim 1, further comprising the step of determining a set of motion compensation factors from the one or more periods of minimal motion.

11. The method as recited in claim 1, further comprising the step of determining two or more gating points from the one or more periods of minimal motion.

12. The method as recited in claim 1, further comprising the step of validating the one or more periods of minimal motion.

13. A computer program, provided on one or more computer readable media, for identifying one or more periods of minimal motion, comprising:

a routine for acquiring at least one set of electrical data representative of cardiac motion, at least one set of non-electrical data representative of cardiac motion, and one or more sets of motion data representative of respiratory organ motion;

a routine for generating a set of multi-input motion data comprising the set of electrical data representative of cardiac motion, the set non-electrical data representative of cardiac motion, and the one or more sets of data representative of respiratory organ motion; and a routine for extracting one or more periods of minimal motion for one of the heart and the respiratory organ from the set of multi-input motion data.

14. The computer program, as recited in claim 13, wherein the one or more sets of data representative of respiratory motion comprise at least one of a set of electrical data representative of respiratory motion and a set of non-electrical data representative of respiratory motion.

15. The computer program, as recited in claim 13, wherein the routine for generating the set of multi-input motion data includes one or more sets of motion data for one or more proximate organs in the set of multi-input motion data.

16. The computer program, as recited in claim 13, wherein the routine for acquiring measures a set of electrical data representative of cardiac motion using electrical sensors.

17. The computer program, as recited in claim 13, wherein the routine for acquiring measures a set of non-electrical data representative of cardiac motion using mechanical sensors.

18. The computer program, as recited in claim 13, wherein the routine for acquiring measures a set of electrical data representative of respiratory motion using electrical sensors.

19. The computer program, as recited in claim 13, wherein the routine for acquiring measures a set of non-electrical data representative of respiratory motion using mechanical sensors.

20. The computer program, as recited in claim 13, wherein the routine for acquiring measures one of cardiac motion and respiratory motion from one or more images.

21. The computer program, as recited in claim 20, wherein the one or more images are derived from one of pre-acquisition image data, unreconstructed acquisition image data, and reconstructed acquisition image data.

22. The computer program, as recited in claim 13, comprising a routine for determining a set of motion compensation factors from the one or more periods of minimal motion.

23. The computer program, as recited in claim 13, comprising a routine for determining two or more gating points from the one or more periods of minimal motion.

24. The computer program, as recited in claim 13, comprising a routine for validating the one or more periods of minimal motion.

25. An imaging system, comprising:

means for acquiring at least one set of electrical data representative of cardiac motion, at least one set of non-electrical data representative of cardiac motion, and one or more sets of data representative of respiratory organ motion;

means for generating a set of multi-input motion data comprising the set of electrical data representative of cardiac motion, the set non-electrical data representative of cardiac motion, the one or more sets of motion data representative of respiratory organ motion; and means for extracting one or more periods of minimal motion for one of the heart and the respiratory organ from the set of multi-input motion data.

26. An imaging system, comprising:

an imager configured to generate a plurality of signals representative of at least one of a heart and a respiratory organ;

data acquisition circuitry configured to acquire the plurality of signals;

data processing circuitry configured to receive the plurality of signals;

system control circuitry configured to operate at least one of the imager and the data acquisition circuitry;

an operator workstation configured to communicate with the system control circuitry and to receive at least the processed plurality of signals from the data processing circuitry;

one or more sensor-based motion measurement systems configured to measure electrical activity indicative of the motion of the heart;

one or more sensor-based motion measurement systems configured to measure non-electrical activity indicative of the motion of the heart; and one or more sensor-based motion measurement systems configured to measure electrical or non-electrical activity indicative of the motion of the respiratory organ;

wherein one or more of the data processing circuitry and operator workstation are configured to extract one or more periods of minimal motion for one of the heart and the respiratory organ from a set of multi-input motion data comprising at least a set of electrical data representative of cardiac motion, at least a set of non-electrical data representative of cardiac motion, and a set of electrical or non-electrical data representative of respiratory motion acquired by the respective sensor-based motion measurement systems.

27. The imaging system as recited in claim 26, wherein a sensor-based motion measurement systems configured to measure non-electrical activity indicative of the motion of the heart and a sensor-based motion measurement systems configured to measure non-electrical activity indicative of the motion of the respiratory organ are the same.

* * * * *